(12) United States Patent
Boucher, Jr. et al.

(10) Patent No.: US 7,737,122 B2
(45) Date of Patent: Jun. 15, 2010

(54) SPINOSYN FUMIGANTS

(75) Inventors: Raymond E. Boucher, Jr., Lebanon, IN (US); James E. Dripps, Carmel, IN (US); Mark Hertlein, Indianapolis, IN (US)

(73) Assignee: Dow AgroScience LLC, Indianapolis, IN (US)

( * ) Notice: Subject to any disclaimer, the term of this patent is extended or adjusted under 35 U.S.C. 154(b) by 184 days.

(21) Appl. No.: 11/805,756

(22) Filed: May 24, 2007

(65) Prior Publication Data

US 2007/0274924 A1 Nov. 29, 2007

Related U.S. Application Data

(60) Provisional application No. 60/808,510, filed on May 25, 2006, provisional application No. 60/808,372, filed on May 25, 2006.

(51) Int. Cl.
*A61K 31/70* (2006.01)
(52) U.S. Cl. .................................................. 514/28
(58) Field of Classification Search .................... 514/28
See application file for complete search history.

(56) References Cited

U.S. PATENT DOCUMENTS

| | | | |
|---|---|---|---|
| 4,382,077 A | 5/1983 | Buchbinder | |
| 5,657,574 A * | 8/1997 | Kandathil et al. | 43/125 |
| 6,419,898 B1 * | 7/2002 | Flashinski et al. | 424/40 |
| 6,927,210 B1 * | 8/2005 | Thompson et al. | 514/28 |
| 2004/0248824 A1 * | 12/2004 | Snyder | 514/28 |

FOREIGN PATENT DOCUMENTS

WO    WO 03/030644 A1    4/2003

OTHER PUBLICATIONS

Ebert, Timothy A. et al. "Comparing greenhouse sprayers: The dose-transfer process" Pest Management Sciences, 60(5), 507-513 CODEN: PMSCF; ISSN: 1526-498X, 204, XP002573174; p. 507, the abstracat; p. 507, paragraph 1; p. 508, left-hand column, last paragraph; table 2; p. 609, left-hand column, paragraph 2-paragraph 4 tables 3, 5, 6.

Munthali D C et al: "Factors Affecting the Biological Efficiency of Small Pesticide.Droplets Against Tetranychus-Urticae Eggs" Pesticide Sciences, vol. 17, No. 2, 1986, pp. 115-164, XP002573447 ISSN: 031-613X p. 155, the abstract; p. 155, paragraph 1 - paragraph 2; figure 1 p. 161, last paragraph.

Himel C M: "The Optimum Size for Insecticide Spray Droplets" Journal of Economic Entomology, Entomological Society of America, Landham, MD, US, vol. 62, No. 4, 1 Jan. 1969, pp. 919-925, XP002027748 ISSN: 0022-0493 p. 919.

* cited by examiner

*Primary Examiner*—Elli Peselev
(74) *Attorney, Agent, or Firm*—Carl D. Corvin; Donald R. Stuart

(57) ABSTRACT

Methods of controlling arthropod pests by dispersing spinosyn compositions in the form of aerosols, fogs, smokes, or vapors are disclosed.

18 Claims, No Drawings

SPINOSYN FUMIGANTS

CROSS-REFERENCE TO RELATED APPLICATIONS

This Application is a Non-Prov of Prov (35 USC 119(e)) application 60/808,510 filed on May 25, 2006. This Application is a Non-Prov of Prov (35 USC 119(e)) application 60/808,372 filed on May 25, 2006.

BACKGROUND

One commonly used method for eliminating pests is fumigation. Fumigants are widely used for the disinfestation, and protection against infestation, that is required to protect greenhouse plants, particulate materials (such as grain) and other stored produce (such as tobacco and foodstuff), and spaces (such as buildings). However, because of the need for high volatility in fumigant use, only a small number of chemicals are routinely used.

The term "fumigant" as used herein refers to an insecticide composition that can be volatilized in the form of ultra small volume droplets (smokes) or vapors to control pests in storage bins, buildings, greenhouses, ships, rail cars, stored products, on foods, plants, other living organisms, or in any closed areas which are prone to attack by pests, i.e., pest infestation. The term "fumigation" refers to the use of such dispersed insecticide compositions to control pests.

Droplet size determines how long pesticide droplets remain suspended in the air, the number of droplets that will be produced from a given volume of pesticide and the size of the treated surface or area that will be covered by each droplet. The following categories should be distinguished:

a. Coarse sprays, with droplets measuring 400 microns or more in diameter;
b. Fine sprays, with droplets of from 100 to 400 microns in diameter;
c. Mists, with droplets from 50 to 100 microns;
d. Aerosols, fogs, and ultra-low volume (ULV) fogs or smokes with particles or droplets ranging from 0.1 to 50 microns in diameter (which are produced by injection of the pesticide into blasts of hot air (thermal fog), mixing with a liquefied gas and released through a small orifice (aerosol), atomized through very fine nozzles, or spun off high-speed rotors);
f. Vapors, in which all particles are less than 0.001 microns in diameter (produced by heat generators).
g. Gasses.

DESCRIPTION OF THE INVENTION

The present invention is directed to a fumigation method utilizing one or more spinosyn compounds.

In one embodiment the invention is directed to a fumigation method utilizing a spinosyn composition dispersed in the form droplets or particles having a diameter in the range of 0.1 to 50 microns.

A more specific embodiment the invention provides a method for disinfesting and protecting plants or plant products which comprises: confining the plants or plant products within an enclosed space and dispersing a spinosyn composition in the form of droplets or particles having a diameter in the range of 0.1 to 50 microns within said space.

Also provided is a method for protecting stored products which comprises confining the stored products within an enclosed space and dispersing in said space, in the form of droplets or particles having a diameter in the range of 0.1 to 50 microns, a composition comprising spinosad and a liquid carrier.

The spinosyn composition used in carrying out the present invention is preferably spinosad or spinetoram, or an organic soluble salt thereof, dissolved or suspended in an inert liquid carrier.

Spinosyn compounds consist of a 5,6,5-tricylic ring system, fused to a 12-membered macrocyclic lactone, a neutral sugar (rhamnose), and an amino sugar (forosamine) (see Kirst et al. (1991)). Natural spinosyn compounds may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931, 5,670,364, 5,591,606, 5,571,901, 5,202,242, 5,767,253, 5,840,861, 5,670,486 and 5,631,155. Derivatives of natural spinosyn compounds, sometimes referred to as spinosoids, are disclosed in U.S. Pat. No. 6,001,981. Spinosyns can be isolated in the form of salts that are also useful in the methods of this invention. The salts are prepared using standard procedures for salt preparation. For example, spinosyns can be neutralized with an appropriate acid to form acid addition salts. Representative suitable acid addition salts include salts formed by reaction with either an organic or inorganic acid, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids. As used herein, the term "spinosyn" includes spinosoids and acid addition salts.

Spinosad is an insecticide produced by Dow AgroSciences (Indianapolis, Ind.) that is comprised mainly of approximately 85% spinosyn A and approximately 15% spinosyn D. Spinosyns A and D are natural products produced by fermentation of *Saccharopolyspora spinosa*, as disclosed in U.S. Pat. No. 5,362,634. Spinosad is an active ingredient of several insecticidal formulations available commercially from Dow AgroSciences, including the TRACER, SUCCESS, SPINTOR, and CONSERVE insect control products. For example, the TRACER product is comprised of about 44% to about 48% spinosad (w/v), or about 4 pounds of spinosad per gallon. Spinosyn compounds in granular and liquid formulations have established utility for the control of arachnids, nematodes, and insects, in particular *Lepidoptera, Thysanoptera*, and *Diptera* species. Because spinosyns are large molecules with low volatility, their utility as fumigants was previously unsuspected.

Other spinosyn compounds of particular interest for practice of the present invention are 5,6-dihydro-3'ethoxy spinosyn J and 3'-ethoxy spinosyn L. These two compounds are disclosed as examples A25 and A38 in U.S. Pat. No. 6,001,981. They are derivatives of natural spinosyn compounds spinosyn J and spinosyn L.

(I)

[Chemical structure of spinosyn showing positions 1-21 with substituents R1', R2', R3', R4', R5', R6', R7']

| Factor | R1' | R2' | R3' | R4' | R5' | R6' | R7' |
|---|---|---|---|---|---|---|---|
| Spinosyn J | H | $CH_3$ | $CH_3$ / $(CH_3)_2N$—[sugar]—O | $C_2H_5$ | $CH_3$ | H | $CH_3$ |
| Spinosyn L | $CH_3$ | $CH_3$ | $CH_3$ / $(CH_3)_2N$—[sugar]—O | $C_2H_5$ | $CH_3$ | H | $CH_3$ |

Spinetoram (previously known as DE-175) is a mixture of 5,6-dihydro-3'ethoxy spinosyn J (major component) and 3'-ethoxy spinosyn L being developed by Dow AgroSciences. The mixture can be prepared by ethoxylating a mixture of spinosyn J and spinosyn L, followed by hydrogenation. The 5,6 double bond of Spinosyn J and its 3'-ethoxy is hydrogenated much more readily than that of spinosyn L and its 3'-ethoxy derivative, due to steric hindrance by the methyl group at C-5 in spinosyn L and its 3'-ethoxy derivative.

Surprisingly, spinosyn compositions can be dispersed in adequate concentrations as ULV aerosols or fogs to effectively control pests using conventional fumigation devices, e.g. ULV foggers and cold misters, thermal foggers, combustible fumigation products (such as smoke canisters or coils like mosquito coils) and thermal vaporizers, such as foggers and mat type devices.

Spinosyn compositions used in the present invention can be solutions or emulsions of a spinosyn or an organic soluble salt of spinosyn in a non-aqueous solvent. Examples of suitable non-aqueous solvents are alkylalcohols having 1 to 10 carbon atoms such as methyl alcohol, ethyl alcohol, n-propyl alcohol, isopropyl alcohol, n-butyl alcohol, sec-butyl alcohol, tert-butyl alcohol, isobutyl alcohol, amyl alcohol, hexyl alcohol, heptyl alcohol, octyl alcohol, nonylalcohol, decyl alcohol, etc.; hydrocarbon solvents such as hexane, octane, cyclopentane, benzene, toluene, xylol, etc.; halogenated hydrocarbon solvents such as carbon tetrachloride, trichloroethylene, tetrachloroethane, dichlorobenzene, etc.; ether solvents such as ethylether, butylether, ethylene glycol diethylether, ethylene glycol monoethylether, etc.; ketone solvents such as acetone, methylethylketone, methylpropylketone, methylamylketone, cyclohexane, etc.; ester solvents such as ethyl formate, methyl acetate, propyl acetate, phenyl acetate, ethylene glycol monoethylether acetate; etc.; alcohol solvents such as diacetone alcohol, etc.; and high-boiling hydrocarbon solvents.

ULV foggers, also known as aerosol generators or cold foggers, since no heating of the formulation is necessary, and thermal foggers in which the pesticide is injected into blasts of hot air, are suitable for use in practicing the invention, are well known in the art, and are available commercially, for example, from Curtis Dyna-Fog Ltd., PO Box 297, Westfield Ind. uu46074, United States http://www.dynafog.com, and Industrial Chemical Cleaner, 6333 Sidney Street, Houston Tex., 777021, hhttp://www.iccfoggers.com/index.htm.

U.S. Pat. No. 4,871,115, and discloses a smoke generating apparatus suitable for use in practicing the present invention.

U.S. Pat. No. 4,777,032 discloses a combustible fumigation device suitable for use in carrying out the present invention. The device comprises paper into which a pesticide has been incorporated. The paper is burnt to disseminate the pesticide. To ensure an efficient and rapid dissemination by means of a large volume of combustion gas containing only a little smoke and originating from a special combustion reaction at a limited temperature so as not to decompose the active compound, this paper is a nitrocellulose-based paper in which the proportion of nitrogen is greater than 5% and in which the fibers consist of a mixture of cellulose and nitrocellulose fibers, this mixture comprising at least 18% of cellulose fibers and the active compound having a decomposition temperature above 130.degree. C.

Combustible coils are another known method for vaporizing materials (e.g. pesticides, incense, etc.) Representative patents describing combustible coils are U.S. Pat. Nos. 3,248,287, 3,723,615, 3,819,823, 4,144,318, 5,657,574, and 6,419,898. These devices are coils of slowly burnable solid material that contain an insect control ingredient such as a repellent, an insecticide, or an insect growth regulator. When they burn, heat vaporizes (and thereby disperses) the insect control ingredient. Small amounts of smoke also help to disperse the insect control ingredient. Such devices are one means conventionally used to control mosquitoes. Mosquito coils are often used to knock down or repel flying insects in living quarters. Traditional mosquito coil compositions include approximately 25% or more of a residue from preparing pyrethrum known as pyrethrum marc, as it is thought this material is a necessary ingredient to produce an acceptable mosquito coil. In addition to the pyrethrum marc, the prime burning agent or fuel used for mosquito coils is coconut shell flour, tabu powder, sawdust, ground leaves, ground bark, starch, etc.

Thermal vaporizers include those of the mat type wherein a mat impregnated with an insecticidal solution is used as placed on a heat plate to vaporize the insecticide into the ambient air. See U.S. Pat. Nos. 6,031,967 6,551,560. Such devices are also conventionally used in mosquito control.

In the case where an insecticide coil is used, the inert support can be, for example, pyrethrum marc compound, Tabu powder (or *Machilus thumbergii* leaf powder), pyrethrum stem powder, cedar leaf powder, sawdust (such as pine sawdust), starch and coconut shell powder. The dose of active ingredient can then be 0.03% to 1% by weight. In the case where an incombustible fibrous support (mat) is used, the dose of active material can be 0.03% to 95% by weight.

The invention can be used, for example, to protect stored grain, or stored foods such as flour or meal or animal feed.

In one embodiment, the present invention provides a method of disinfesting agricultural products such as tobacco by fumigation with a spinosyn. A major pest of stored tobacco and tobacco products is the cigarette beetle, *Laisoderma serricorne*. During the past 50 years, toxic fumigants such as hydrogen cyanide, methyl bromide, and hydrogen phosphide have been used to fumigate tobacco and other agricultural products for control of the cigarette beetle and other stored product insects. Usage of these and other fumigants has become increasingly restricted during the past several years because of regulatory agencies' concern with worker exposure to pesticides, pesticide residue on agricultural products, fumigant flammability, and contamination of air and water.

The fumigation method of this invention can be used to control pests of the Phylum Arthropoda.

In one embodiment, the invention can be used to control pests of the Subphylum Hexapoda. More specifically, the invention can be used to control pests of the Class Insecta. For example, the fumigation method of this invention can be used to control Coleoptera (beetles), Dermaptera (earwigs), Dictyoptera (cockroaches), Diptera (true flies), Hemiptera (true bugs), Homoptera (aphids, scales, whiteflies, leafhoppers), Hymenoptera (ants, wasps, and bees), Isoptera (termites), Lepidoptera (moths and butterflies), Mallophaga (chewing lice), Orthoptera (grasshoppers, locusts, and crickets), Phthiraptera (sucking lice), Siphonaptera (fleas), and Thysanoptera (thrips).

In another embodiment, the fumigation method of this invention can be used to control pests of the Subphylum Chelicerata. More specifically, the fumigation method of this invention can be used to control pests of the Class Arachnida. For example, the fumigation method of this invention can be used to control Acarina (mites and ticks).

EXAMPLES 1-10

Lab trials were conducted to test spinosad and spinetoram for insecticidal activity via thermal fogger delivery. Test insects included *Aedes aegypti*, yellow fever mosquito; *Drosophila melanogaster* fruit fly; *Musca domestica* house fly; and *Plodia interpunctella*, Indian meal moth.

Test Chambers. The test chambers were developed by suspending polyethylene (PE) bags from a PVC pipe support structure. The bags were 3 mil PE pallet covers measuring 48"W×48"D×102"H (ULINE product # S-8366) with an enclosed internal volume of approximately 100 $ft^3$. The chambers were sealed at floor level to a flat 4 mil PE sheet. Five chambers were made to accommodate 4 treatment replicates and one solvent blank control. All chambers were used once per application and then discarded.

Holding Cages. For yellow fever mosquito, house fly, and Indian meal moth, holding cages were made from 18×16 mesh standard aluminum insect screening. A circular cage was made to measure 3.5" in diameter and 5.5" high. The floor and ceiling of the holding cages were sterile acrylic Petri dish covers and bottoms. In each holding cage insects were supplied with a 10% sucrose solution from a 7.5 ml glass vial and sterile cotton wick. For fruit flies, white polyester mosquito netting with a 0.8 mm mesh opening was glued to the lid of a fruit jar and placed into the bottom of the Petri dish to create a suitable holding cage. Sugar water was provided from a 2 ml vial.

Thermal Fogger Device. A Dynafog Trailblazer Model 2600E,series 3 thermal fogger was used for application. The fogger is designed to deliver up to 19 liters of formulation per hour with a particle size in the range of 0.5-50 microns. It is designed for application to enclosed spaces greater than 500 $ft^3$. As a result, the fogger was modified to deliver smaller volumes which could be adjusted to accommodate the 100 $ft^3$ test chamber.

All hoses that delivered the formulation were reduced to 3.2 mm OD 2.0 mm ID nylon tubing. The formulation tank was reduced to a 250 ml HDPE bottle with appropriate fittings to accommodate the tubing. The fogger on/off switch was bypassed and replaced with a manual toggle switch. This configuration was calibrated with a needle valve adjustment to deliver approximately 4.0 liters per hour.

Insect Handling. Collection of Indian meal moth was achieved by selecting carbon dioxide-anesthetized individuals from culture jars. Adult yellow fever mosquitoes, house flies, and fruit flies were aspirated from culture jars into a 50 ml holding jar and then anaesthetized with carbon dioxide and collected. All insects were allowed to recover from anesthesia for at least 1 hour before testing began. Fifty adults were used for each replicate. Any insects that were dead or injured from handling were noted as pre-treatment mortality data.

Application. The formulation used in the testing consisted of 1.1% spinosad (90% purity), 1.5% Isopropyl Myristate (Cognis Corporation; Cincinnati, Ohio), 4.0% Emersol 213 (Cognis Corporation), and 93.4% Exxsol D80 (ExxonMobil; Houston, Tex.) or 1.2% spinetoram (81% purity), 1.5% Isopropyl Myristate (Cognis Corporation), 4.0% Emersol 213 (Cognis Corporation), and 93.3% Exxsol D80 (ExxonMobil). A blank treatment with just the solvent mixture was one of the control treatments. The other control treatment was the absence of active ingredient and solvent.

All applications were done at room temperature of approximately 71-72° F. All insect holding cages were positioned from hangers in the corners of the test chambers just prior to treatment, or in the case of the fruit flies, the test holding cages were put on the floor.

The fogger was charged and run to clean out lines with solvent only. The flow rates were adjusted after calibration to deliver approximately 1 ml per second. The following steps 1-11 are considered one trial for one formulation:

1. The fogger was turned on and allowed to warm up to temperature (3-5 minutes).
2. The toggle valve was opened to allow the formulation to charge the line before each treatment run (~50 ml).
3. The amount of formulation in the formulation tank was weighed on a Sartorius BL1500 scale and then reattached to the fogger.

4. The fogger was positioned in front of a rectangular opening cut into the treatment chamber. A digital timer was turned on and the toggle valve opened to apply the formulation or solvent.
5. After 5 to 7 seconds, the toggle valve was closed and the fogger turned off.
6. The rectangular opening was immediately sealed with packing tape.
7. The formulation tank was weighed and the difference in mass was recorded as was the application time in seconds.
8. The tank was reattached and steps 4-7 were repeated for the next three treatment chambers.
9. When the four treatment chambers were done, the fogger was flushed with clean solvent (~50 ml) to remove formulation from the fogger.
10. A new formulation tank with solvent only was then reattached after weighing.
11. The fogger was charged with solvent and then steps 3-7 were performed for the solvent blank treatment chamber.

The untreated control test cages were kept in an adjacent room under identical temperature and light conditions.

Efficacy evaluation. The effectiveness of the applications was recorded at 1 hour, 4 hours, 18 hours, and 24 hours. The number of live and dead insects was recorded at each interval for all treatments, solvent control, and the untreated control test cages.

Example 1

Control of adult house flies, *Musca domestica*, with spinosad.

| Treatment | Solvent volume | Spinosad Concentration ($g/m^3$) | Percent mortality 1 hr | 4 hr | 18 hr* | 24 hr* |
|---|---|---|---|---|---|---|
| Untreated | 0 ml | 0 | 0 | 0 | — | — |
| Solvent blank | 8.8 ml | 0 | 0 | 16 | — | — |
| Spinosad | 7.3 ml | 0.026 | 14 | 76 | — | — |
| Spinosad | 9.5 ml | 0.034 | 14 | 90 | — | — |
| Spinosad | 9.0 ml | 0.032 | 26 | 90 | — | — |
| Spinosad | 8.2 ml | 0.029 | 24 | 94 | — | — |

*high mortality occurred in the untreated and solvent blank treatments.

Example 2

Control of adult fruit flies, *Drosophila melanogaster*, with spinosad.

| Treatment | Solvent volume | Spinosad Concentration ($g/m^3$) | Percent mortality 1 hr | 4 hr | 18 hr | 24 hr |
|---|---|---|---|---|---|---|
| Untreated | 0 ml | 0 | 0 | 0 | 0 | 0 |
| Solvent blank | 8.8 ml | 0 | 0 | 2 | 2 | 2 |
| Spinosad | 7.3 ml | 0.026 | 12 | 100 | 100 | 100 |
| Spinosad | 9.5 ml | 0.034 | 2 | 100 | 100 | 100 |
| Spinosad | 9.0 ml | 0.032 | 4 | 100 | 100 | 100 |
| Spinosad | 8.2 ml | 0.029 | 0 | 100 | 100 | 100 |

Example 3

Control of 2 day old adult Indian meal moths, *Plodia interpunctella*, with spinosad.

| Treatment | Solvent volume | Spinosad concentration ($g/m^3$) | Percent mortality 1 hr | 4 hr | 18 hr | 24 hr |
|---|---|---|---|---|---|---|
| Untreated | 0 ml | 0 | 0 | 0 | 0 | 0 |
| Solvent blank | 8.2 ml | 0 | 0 | 0 | 2 | 2 |
| Spinosad | 6.8 ml | 0.024 | 4 | 4 | 51 | 61 |
| Spinosad | 8.9 ml | 0.031 | 2 | 4 | 41 | 47 |
| Spinosad | 11.0 ml | 0.039 | 4 | 10 | 83 | 88 |
| Spinosad | 9.1 ml | 0.032 | 0 | 8 | 58 | 60 |

Example 4

Control of 4 day old adult Indian meal moths, *Plodia interpunctella*, with spinosad.

| Treatment | Volume | Spinosad concentration ($g/m^3$) | Percent mortality 1 hr | 4 hr | 18 hr | 24 hr |
|---|---|---|---|---|---|---|
| Untreated | 0 ml | 0 | 0 | 0 | 3 | 5 |
| Solvent blank | 2.9 ml | 0 | 0 | 6 | 30 | 30 |
| Spinosad | 5.4 ml | 0.019 | 2 | 31 | 96 | 100 |
| Spinosad | 5.7 ml | 0.020 | 2 | 36 | 96 | 98 |
| Spinosad | 8.1 ml | 0.029 | 11 | 56 | 100 | 100 |
| Spinosad | 7.9 ml | 0.028 | 7 | 40 | 98 | 100 |

Example 5

Control of adult yellow fever mosquitoes, *Aedes aegypti*, with spinosad.

| Treatment | Volume | Spinosad concentration ($g/m^3$) | Percent mortality 1 hr | 4 hr | 18 hr | 24 hr |
|---|---|---|---|---|---|---|
| Untreated | 0 ml | 0 | 0 | 0 | 0 | 0 |
| Solvent blank | 8.6 ml | 0 | 0 | 0 | 0 | 0 |
| Spinosad | 10.2 ml | 0.036 | 0 | 7 | 93 | 100 |
| Spinosad | 11.7 ml | 0.041 | 0 | 47 | 100 | 100 |
| Spinosad | 12.6 ml | 0.044 | 0 | 100 | 100 | 100 |
| Spinosad | 12.6 ml | 0.044 | 0 | 100 | 100 | 100 |

Example 6

Control of adult yellow fever mosquitoes, *Aedes aegypti*, with spinosad.

| Treatment | Volume | Spinosad concentration ($g/m^3$) | Percent mortality 1 hr | 4 hr | 18 hr | 24 hr |
|---|---|---|---|---|---|---|
| Untreated | 0 ml | 0 | 0 | 5 | 10 | 10 |
| Solvent blank | 8.8 ml | 0 | 0 | 10 | 14 | 24 |
| Spinosad | 7.3 ml | 0.026 | 12 | 48 | 96 | 100 |
| Spinosad | 9.5 ml | 0.034 | 2 | 100 | 100 | 100 |
| Spinosad | 9.0 ml | 0.032 | 4 | 97 | 100 | 100 |
| Spinosad | 8.2 ml | 0.029 | 0 | 62 | 100 | 100 |

Example 7

Control of adult house flies. *Musca domestica*, with spinetoram.

| Treatment | Solvent volume | Spinetoram concentration ($g/m^3$) | Percent mortality | | | |
|---|---|---|---|---|---|---|
| | | | 1 hr | 4 hr | 18 hr | 24 hr |
| Untreated | 0 ml | 0 | 0 | 0 | 0 | 16 |
| Solvent blank | 7.5 ml | 0 | 0 | 0 | 0 | 14 |
| Spinetoram | 6.7 ml | 0.024 | 4 | 84 | 100 | 100 |
| Spinetoram | 6.7 ml | 0.024 | 2 | 84 | 100 | 100 |
| Spinetoram | 5.7 ml | 0.020 | 0 | 0 | 64 | 80 |
| Spinetoram | 11.0 ml | 0.039 | 0 | 86 | 100 | 100 |

Example 8

Control of adult fruit flies, *Drosophila melanogaster.*, with spinetoram.

| Treatment | Solvent volume | Spinetoram concentration ($g/m^3$) | Percent mortality | | | |
|---|---|---|---|---|---|---|
| | | | 1 hr | 4 hr | 18 hr | 24 hr |
| Untreated | 0 ml | 0 | 0 | 0 | 0 | 0 |
| Solvent blank | 7.5 ml | 0 | 0 | 0 | 8 | 12 |
| Spinetoram | 6.7 ml | 0.024 | 0 | 88 | 100 | 100 |
| Spinetoram | 6.7 ml | 0.024 | 0 | 70 | 100 | 100 |
| Spinetoram | 5.7 ml | 0.020 | 0 | 16 | 76 | 90 |
| Spinetoram | 11.0 ml | 0.039 | 0 | 72 | 100 | 100 |

Example 9

Control of 2 day old adult Indian meal moths, *Plodia interpunctella*, with spinetoram.

| Treatment | Solvent volume | Spinetoram concentration ($g/m^3$) | Percent mortality | | | |
|---|---|---|---|---|---|---|
| | | | 1 hr | 4 hr | 18 hr | 24 hr |
| Untreated | 0 ml | 0 | 0 | 0 | 0 | 2 |
| Solvent blank | 9.0 ml | 0 | 0 | 0 | 2 | 2 |
| Spinetoram | 4.2 ml | 0.015 | 0 | 0 | 6 | 8 |
| Spinetoram | 5.8 ml | 0.020 | 2 | 2 | 14 | 22 |
| Spinetoram | 4.6 ml | 0.016 | 0 | 0 | 18 | 31 |
| Spinetoram | 5.7 ml | 0.020 | 0 | 0 | 16 | 24 |

Example 10

Control of 4 day old adult Indian meal moths, *Plodia interpunctella*, with spinetoram.

| Treatment | Solvent volume | Spinetoram concentration ($g/m^3$) | Percent mortality | | | |
|---|---|---|---|---|---|---|
| | | | 1 hr | 4 hr | 18 hr | 24 hr |
| Untreated | 0 ml | 0 | 0 | 0 | 0 | 0 |
| Solvent blank | 11.3 ml | 0 | 0 | 0 | 2 | 2 |
| Spinetoram | 8.7 ml | 0.031 | 0 | 0 | 4 | 38 |
| Spinetoram | 7.8 ml | 0.028 | 1 | 1 | 10 | 70 |
| Spinetoram | 9.0 ml | 0.032 | 0 | 0 | 9 | 42 |
| Spinetoram | 7.9 ml | 0.028 | 0 | 0 | 11 | 41 |

Example 11

Control of adult yellow fever mosquitoes, *Aedes aegypti*, with spinetoram.

| Treatment | Solvent volume | Spinetoram concentration ($g/m^3$) | Percent mortality | | | |
|---|---|---|---|---|---|---|
| | | | 1 hr | 4 hr | 18 hr | 24 hr |
| Untreated | 0 ml | 0 | 0 | 0 | 0 | 0 |
| Solvent blank | 9.3 ml | 0 | 0 | 0 | 0 | 0 |
| Spinetoram | 8.1 ml | 0.029 | 3 | 97 | 100 | 100 |
| Spinetoram | 8.2 ml | 0.029 | 0 | 53 | 100 | 100 |
| Spinetoram | 7.3 ml | 0.025 | 0 | 94 | 100 | 100 |

Formulation Example 1

Combustible Coil

First, 0.5 g of spinetoram is dissolved in 20 ml of acetone. The solution is uniformly stirred and mixed with 99.4 g of a carrier for mosquito coil (a mixture of camphor powder:lees powder:wood meal at 4:3:3). Thereto is added 120 ml of water and the mixture was well kneaded, followed by shaping and drying to obtain a combustible coil.

Formulation Example 2

Coil

First, 0.5 g of each of spinetoram is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring. The mixture is well kneaded with 120 ml of water, molded and dried to give a combustible coil.

Formulation Example 3

Electric Mat

Acetone is added to 0.5 g of spinetoram and 0.4 g of pipenyl butoxide to dissolve the ingredients to prepare a solution in an amount of 10 ml in total. A substrate for electric mat (fibrils of a mixture of cotton linter and pulp which were hardened into a sheet) of 2.5 cm.by 1.5 cm.by 0.3 cm thick is uniformly impregnated with the above solution to obtain an electric mat.

Formulation Example 4

Heat Smoking Agent

First, 100 mg of spinetoram is dissolved in a suitable amount of acetone. A porous ceramic sheet of 4.0 cm.by 4.0 cm.by 1.2 cm thick is impregnated with the resulting solution to obtain a heat smoking agent.

Electrically heated mats impregnated with spinosad have demonstrated the ability to control adult mosquitoes when tested in accordance with standard protocols (SANS Method 6136).

All patents and publications referred to above are incorporated by reference herein.

We claim:

1. An arthropod pest control method which comprises dispersing in a space where arthropod pest control is desired a composition comprising spinetoram and a liquid carrier, wherein said composition is dispersed in the form of droplets or particles having a diameter of 0.001 microns or less to produce a vapor.

2. The method of claim 1 wherein said composition is dispersed in an enclosed space.

3. A method for disinfesting a space which comprises dispersing in said space a composition comprising spinetoram and a non-aqueous organic solvent in the form of droplets or particles having a diameter of 0.001 microns or less to produce a vapor.

4. The method of claim 1 used to control beetles, cockroaches, or ants.

5. The method of claim 1 used to control flies or moths.

6. The method of claim 2 wherein said space is in a greenhouse.

7. An arthropod pest control method which comprises dispersing in a space where arthropod pest control is desired a composition comprising a spinosyn and a liquid carrier, wherein said composition is dispersed in the form of droplets or particles having a diameter of 0.001 microns or less to produce a vapor.

8. The method of claim 7 wherein said composition is dispersed in an enclosed space.

9. A method for disinfesting a space which comprises dispersing in said space a composition comprising a spinosyn and a non-aqueous organic solvent in the form of droplets or particles having a diameter of 0.001 microns or less to produce a vapor.

10. The method of claim 7 used to control beetles, cockroaches, or ants.

11. The method of claim 7 used to control flies or moths.

12. The method of claim 8 wherein said space is in a greenhouse.

13. An arthropod pest control method which comprises dispersing in a space where arthropod pest control is desired a composition comprising spinosad and a liquid carrier, wherein said composition is dispersed in the form of droplets or particles having a diameter of 0.001 microns or less to produce a vapor.

14. The method of claim 13 wherein said composition is dispersed in an enclosed space.

15. A method for disinfesting a space which comprises dispersing in said space a composition comprising spinosad and a non-aqueous organic solvent in the form of droplets or particles having a diameter of 0.001 microns or less to produce a vapor.

16. The method of claim 13 used to control beetles, cockroaches, or ants.

17. The method of claim 13 used to control flies or moths.

18. The method of claim 14 wherein said space is in a greenhouse.

* * * * *